Jan. 11, 1955 R. J. POMMERT Plant Pat. 1,339
GLADIOLUS PLANT
Filed April 20, 1954
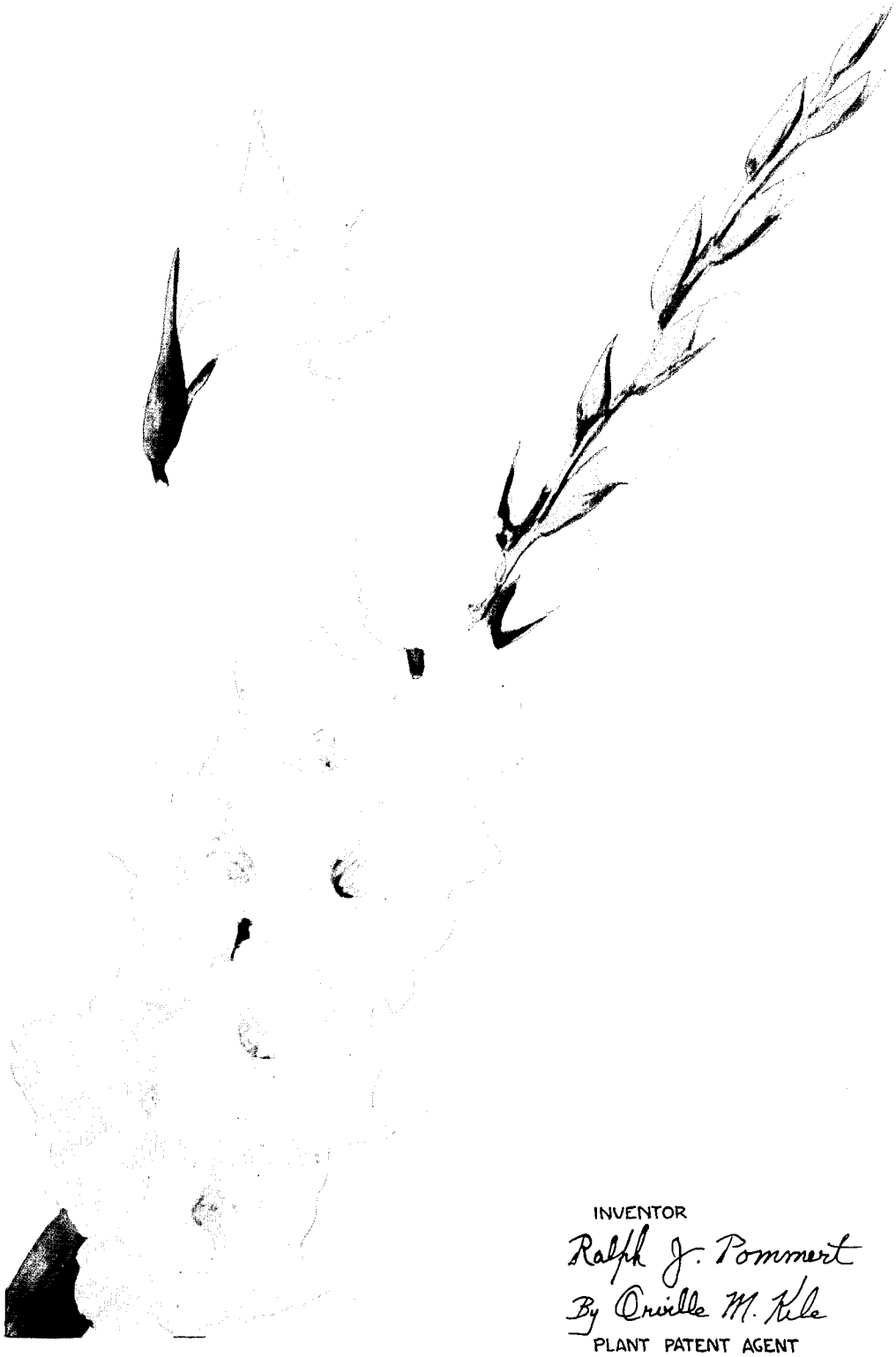
INVENTOR
Ralph J. Pommert
By Orville M. Kile
PLANT PATENT AGENT United States Patent Office Plant Pat. 1,339
Patented Jan. 11, 1955

1,339

GLADIOLUS PLANT

Ralph J. Pommert, Pacific, Wash.

Application April 20, 1954, Serial No. 424,537

1 Claim. (Cl. 47—60)

My present invention relates to a new and improved variety of gladiolus plant which originated from a cross made by me between the varieties Red Charm as the seed parent, and an unnamed seedling as the pollen parent (both unpatented). The new variety originated at my gardens in the State of Washington and I have asexually reproduced the variety at the same location, by natural increase from bulblets. I have observed and tested this new variety through several generations of asexual reproduction and its characteristics appear to be firmly fixed.

This new variety is a very sturdy and vigorous grower, germinates readily, and usually produces good-sized bulbs the first year. It has an unusually large number of florets and buds showing color at one time, as well as a tendency of the buds to stand out from the stem. Notable too is the superiority of the attachment of the florets to the stem, in this respect surpassing almost all other gladiolus varieties in commerce today. No other gladiolus known to me has the same clear scarlet-red color as my new variety, and the light, silvery-white area on the back of the florets distinguishes it from all other red varieties.

The illustration accompanying this specification shows in approximately true colors, a typical spike of bloom of this variety, with a single floret in the upper left-hand corner showing the light area on the back of the petals.

In the following detailed description of the plant and flower, color plate references are to Ridgway's Color Standards and Nomenclature. Other color names indicate the usual dictionary meaning of the term.

*The plant*

Growth: Exceptionally sturdy as compared with the average gladiolus variety. Field-run height of spikes grown under commercial conditions has varied from 49 inches to 70 inches in recorded trials, depending on climate and weather conditions. The average is about 55 inches.

Propagation: Variety germinates easily. Bulblets are better than average in size, producing good-sized bulbs the first year.

Blooming season: Blooms early. Average blooming dates, from large bulbs planted approximately April 20th at this location, fall between August 5th and 20th.

Stems: Straight, stiff, strong and sturdy but not heavy.

Foliage: Upright and broad, measuring approximately 36 inches high and 1½ inches broad.

Corms: Surface somewhat wrinkled, the wrinkles radiating from the basal scar. Skin is yellow and husk ivory-tan merging into reddish-purple at the top.

Spike: Long and slender, the approximate length being 48 inches when cut for commercial cut flowers (leaving at least 4 full leaves on the plant). Spike rises well above foliage, with flower heads averaging 24 inches long. Usually eight florets are fully open at one time, with about 8 or 9 buds showing color at this same time. When florets start to open at the bottom of the spike, the buds all the way to the tip stand out separately rather than tending to overlap as in many other varieties. Attachment of buds and florets to spike is exceptionally good.

*The flower*

The bud:

*Size.*—When just beginning to show color, bud is approximately ⅞ inch long.

*Color.*—Approximately Scarlet-Red (Plate I).

Flower:

*Arrangement.*—Flowers are closely and evenly spaced on the spike and all face in the same direction.

*Form.*—Open; somewhat square in shape, with slightly pointed effect of petals.

*Size.*—Fully opened floret measures 4¾ to 5 inches in diameter, without straightening out tips of petals.

*Fragrance.*—None.

*Keeping qualities.*—Almost the whole spike shows color at one time and therefore the spike will not last as long as those of many other varieties, although the individual florets will keep as well or better than most.

Petals:

*Shape.*—Lightly ruffled edge, with petals reflexing at tips except for the midribs, creating a slightly pointed effect.

*Substance.*—Above average.

*Color.*—In popular terms, the color may be described as a clear red varying from red-scarlet to scarlet-red depending upon soil and climatic conditions. Compared with Ridgway's Color Standards and Nomenclature, the flowers grown under conditions found in this climate are approximately Scarlet-Red (Plate I). Unlike any other red variety known to me, the back to the lower three petals of each floret has a silvery-white area or splotch emerging from the base.

Reproductive organs: Prominent; pistil arises approximately ⅝ inch.

Having thus disclosed my invention, I claim:

The new and distinct variety of gladiolus plant, substantially as herein shown and described, characterized particularly by its sturdy growth; its early blooming season; its exceptionally good germination quality; the excellence of the attachment of the floret and buds to the spike; the regular and compact arrangement of the flower on the spike but with no overlapping of the buds; the large number of florets showing color at one time; and the scarlet-red color of its flower with a distinguishing white area on the back of the three lower petals of each floret.

No references cited.